United States Patent
Kim et al.

(10) Patent No.: US 12,320,879 B2
(45) Date of Patent: Jun. 3, 2025

(54) METHOD AND APPARATUS FOR RECONSTRUCTING AN ELECTRICAL CONDUCTIVITY MAP FROM MAGNETIC RESONANCE IMAGING

(71) Applicant: UIF (University Industry Foundation), Yonsei University, Seoul (KR)

(72) Inventors: Dong-Hyun Kim, Seoul (KR); Kyu-Jin Jung, Seoul (KR)

(73) Assignee: UIF (University Industry Foundation), Yonsei University, Seoul (KR)

(*) Notice: Subject to any disclaimer, the term of this patent is extended or adjusted under 35 U.S.C. 154(b) by 345 days.

(21) Appl. No.: 18/052,808

(22) Filed: Nov. 4, 2022

(65) Prior Publication Data
US 2023/0168328 A1    Jun. 1, 2023

(30) Foreign Application Priority Data
Nov. 26, 2021    (KR) .................. 10-2021-0165765

(51) Int. Cl.
*G01R 33/56*    (2006.01)
*A61B 5/055*    (2006.01)
(Continued)

(52) U.S. Cl.
CPC .......... *G01R 33/5608* (2013.01); *A61B 5/055* (2013.01); *G01R 33/50* (2013.01);
(Continued)

(58) Field of Classification Search
CPC .... G01R 33/5608; G01R 33/50; G01R 33/58; G01R 33/5602; G01R 33/443;
(Continued)

(56) References Cited

U.S. PATENT DOCUMENTS

| | | | |
|---|---|---|---|
| 9,111,334 B2* | 8/2015 | McCollough | ........ A61B 6/5205 |
| 2017/0045601 A1* | 2/2017 | Akhtari | ............... A61B 5/0042 |

(Continued)

FOREIGN PATENT DOCUMENTS

| | | |
|---|---|---|
| CN | 1981700 A | 6/2007 |
| JP | 2021-137534 A | 9/2021 |

(Continued)

OTHER PUBLICATIONS

Jung, Kyu-Jin, et al. "Improving phase-based conductivity reconstruction by means of deep learning-based denoising of phase data for 3T MRI." Magnetic Resonance in Medicine 86.4 (2021): 2084-2094. (Year: 2021).*

(Continued)

*Primary Examiner* — Rishi R Patel
(74) *Attorney, Agent, or Firm* — BROADVIEW IP LAW, PC

(57) ABSTRACT

The exemplary embodiments provides an apparatus and a method for reconstructing an electrical conductivity map which reconstruct an electrical conductivity map for high resolution clinical data with a low SNR by generating virtual magnetic resonance imaging data and ground-truth electrical conductivity map data based on simulated data and adding a noise to the virtual magnetic resonance imaging data to train a previously designed deep learning network.

5 Claims, 13 Drawing Sheets
(7 of 13 Drawing Sheet(s) Filed in Color)

(51) Int. Cl.
*G01R 33/50* (2006.01)
*G01R 33/58* (2006.01)
*G06T 7/00* (2017.01)

(52) U.S. Cl.
CPC ............ *G01R 33/58* (2013.01); *G06T 7/0012* (2013.01); *G06T 2207/10088* (2013.01); *G06T 2207/20081* (2013.01); *G06T 2207/20084* (2013.01); *G06T 2207/30016* (2013.01)

(58) Field of Classification Search
CPC ... G01R 33/4806; A61B 5/055; A61B 5/0042; A61B 5/4064; A61B 5/7203; G06T 7/0012; G06T 2207/10088; G06T 2207/20081; G06T 2207/20084; G06T 2207/30016
See application file for complete search history.

(56) References Cited

U.S. PATENT DOCUMENTS

| | | |
|---|---|---|
| 2019/0059732 A1 | 2/2019 | Kim et al. |
| 2020/0214569 A1 | 7/2020 | Kim |
| 2020/0214570 A1 | 7/2020 | Kim |
| 2021/0365736 A1 | 11/2021 | Kearney et al. |
| 2022/0248973 A1* | 8/2022 | Katscher ............... G06T 11/006 |

FOREIGN PATENT DOCUMENTS

| | | |
|---|---|---|
| KR | 10-2015-0054648 A | 5/2015 |
| KR | 10-1806198 B1 | 12/2017 |
| KR | 10-2019-0028901 A | 3/2019 |
| KR | 10-1995900 B1 | 7/2019 |
| KR | 10-2019-0124994 A | 11/2019 |

OTHER PUBLICATIONS

Inda, Adan Jafet Garcia, et al. "Physics-Coupled Neural Network Magnetic Resonance Electrical Property Tomography (MREPT) for Conductivity Reconstruction." arXiv preprint arXiv:2109.12873 (Sep. 2021). (Year: 2021).*

Hampe, Nils et al. "Investigating the challenges and generalizability of deep learning brain conductivity mapping." Paper. Institute of Physics and Engineering in Medicine. Phys. Med. Biol. 65 (2020) 135001. Jun. 22, 2020 <https://doi.org/10.1088/1361-6560/ab9356>.

Jung, Kyu-jin, et al., "Feasibility study for conductivity reconstructions from spin-echo images using artificial neural network with simulation data in 3T MR system", International Society for Magnetic Resonance in Medicine (ISMRM) 31st annual meeting & exhibition, May 7-12, 2022.

Lee, Mun Bae et al. "High-frequency conductivity at Larmorfrequency in human brain using moving local window multilayer perceptron neural network." Research Article. May 20, 2021. <https://doi.org/10.1371/journal.pone.0251417>.

Gavazzi, Soraya et al. "Deep learning-based reconstruction of in vivo pelvis conductivity with a 3D patch-based convolutional neural network trained on simulated MR data." Full Paper. Department of Radiotherapy, University Medical Center Utrecht, Utrecht, The Netherlands. Mar. 26, 2020.

Mandija, Stefano et al. "Opening a new window on MR-based Electrical Properties Tomography with deep learning." Article. Scientific Reports. Jun. 20, 2019.

Leijsen, Reijer et al. "Combining deep learning and 3D contrast source inversion in MR-based electrical properties tomography." Special Issue Research Article. C.J. Gorter Center for High Field MRI, Leiden University Medical Center, 2333ZA Leiden, The Netherlands. Oct. 9, 2019 <https://doi.org/10.1002/nbm.4211>.

Garcia Inda, Adan Jafet et al. "Physics-Coupled Neural Network Magnetic Resonance Electrical Property Tomography (MREPT) for Conductivity Reconstruction." IEEE Transactions on Image Processing, vol. 31, 2022.

Jung, Kyu-jin, et al., "Feasibility study for conductivity reconstruction using artificial neural network with simulation data in 3 T MR system", The 9th International Congress on Magnetic Resonance Imaging & 26th Annual Scientific Meeting of KSMRM (ICMRI 2021), Nov. 5, 2021.

Office Action for KR 10-2021-0165765 by Korean Intellectual Property Office dated Jan. 19, 2024.

* cited by examiner

FIG. 1
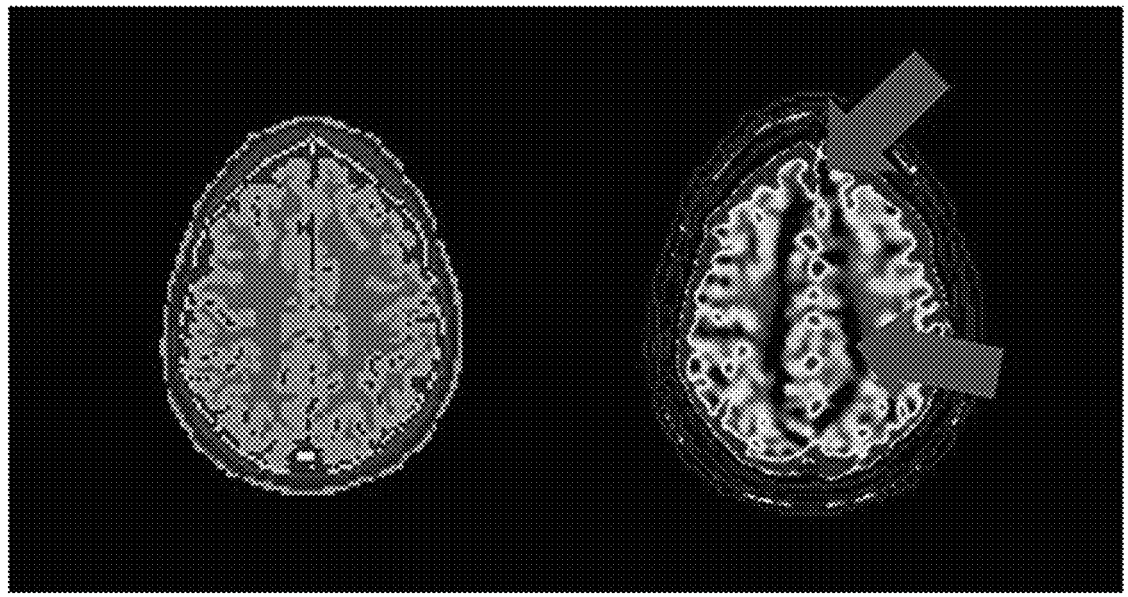
(GROUND-TRUTH) ELECTRICAL CONDUCTIVITY MAP
HELMHOLTZ BASED ELECTRICAL CONDUCTIVITY MAP
FIG. 2
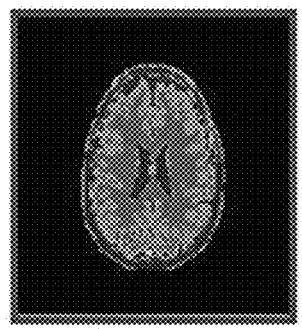
(GROUND-TRUTH) ELECTRICAL CONDUCTIVITY MAP
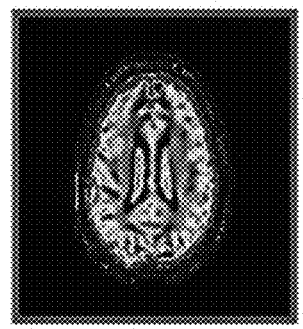
RECONSTRUCTED ELECTRICAL CONDUCTIVITY MAP without noise
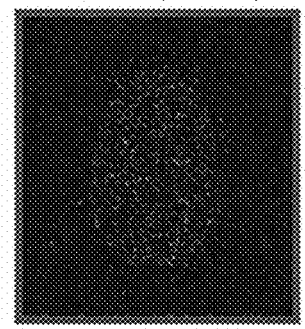
RECONSTRUCTED ELECTRICAL CONDUCTIVITY MAP with noise(SNR=100)

SIMULATED HUMAN PHANTOM AND RF COIL CONFIGURATION

METHOD AND APPARATUS FOR RECONSTRUCTING AN ELECTRICAL CONDUCTIVITY MAP FROM MAGNETIC RESONANCE IMAGING

CROSS-REFERENCE TO RELATED APPLICATIONS

This application claims priority under 35 U.S.C § 119 to Korean Patent Application No. 10-2021-0165765 filed in the Korean Intellectual Property Office on Nov. 26, 2021, the entire contents of which are hereby incorporated by reference.

BACKGROUND

Field

The technical field of the present disclosure relates to an electrical property tomography (EPT) which is a non-invasive imaging technology of measuring electrical properties of a human tissue using a magnetic resonance imaging (MRI) apparatus.

This research was supported by the MSIT (Ministry of Science and ICT), Korea, under the ITRC (Information Technology Research Center) support program (IITP-2022-2020-0-01461) supervised by the IITP (Institute for Information & communications Technology Planning & Evaluation).

This work was also supported by the National Research Foundation of Korea (NRF) grant funded by the Korea government (MSIT) (NRF-2019R1A2C1090635).

Description of the Related Art

The contents described in this section merely provide background information on the present exemplary embodiment but do not constitute the related art.

The electrical property tomography (EPT) is a non-invasive image reconstruction technology which estimates electrical properties (electrical conductivity a and permittivity F) of a human tissue using a magnetic resonance imaging (MRI) apparatus. The electrical properties may be estimated by utilizing radio frequency (RF) magnetic field information which is induced in the body from the MRI device.

RELATED ART DOCUMENT

Patent Document (Patent Document 1) KR 10-1995900 (2019.06.27)
Non-Patent Document
(Non-Patent Document 1) MANDIJA, Stefano, et al. Opening a new window on MR-based Electrical Properties Tomography with deep learning. Scientific reports, 2019, 9.1: 1-9.
(Non-Patent Document 2) LEIJSEN, Reijer, et al. Combining deep learning and 3D contrast source inversion in MR-based electrical properties tomography. NMR in Biomedicine, 2019, e4211.
(Non-Patent Document 3) HAMPE, Nils, et al. Investigating the challenges and generalizability of deep learning brain conductivity mapping. Physics in Medicine & Biology, 2020, 65.13: 135001.
(Non-Patent Document 4) LEE, Mun Bae, et al. High-frequency conductivity at Larmor-frequency in human brain using moving local window multilayer perceptron neural network. Plos one, 2021, 16.5: e0251417.

SUMMARY

A major object of the exemplary embodiments of the present disclosure is to reconstruct an electrical conductivity map for a biological tissue by generating virtual magnetic resonance imaging data and ground-truth electrical conductivity map data based on simulated data and adding a noise to the virtual magnetic resonance imaging data to train a previously designed deep learning network to receive high resolution clinical data with a low SNR.

Other and further objects of the present disclosure which are not specifically described can be further considered within the scope easily deduced from the following detailed description and the effect.

According to an aspect of the present embodiment, an electrical conductivity map reconstruction method includes dividing a magnetic resonance imaging (MRI) for a biological tissue into first magnitude data and first phase data; and generating an electrical conductivity map from the first magnitude data and the first phase data, by an electrical conductivity reconstruction network.

The electrical conductivity reconstruction network is trained by composing a virtual MRI image without a noise based on simulated data; generating a ground-truth electrical conductivity map based on the simulated data; adding a noise to the virtual MRI image; and performing network learning using the virtual MRI image with the added noise and the ground-truth electrical conductivity map.

The simulated data is formed by configuring a simulation environment using a simulation human body phantom and a radio frequency (RF) coil and acquiring data about an RF magnetic field, a current density, and an electrical field without having a noise.

The virtual MRI image without having a noise is acquired by means of a relational expression including a repeated time TR and an echo time TE required to set the RF magnetic field and a contrast and a first relaxation time T1 and a second relaxation time T2 required to produce MR contrast (e.g., T2-w image) for each human brain region.

The ground-truth electrical conductivity map is acquired by a relational equation including the current density and the electric field.

In the adding of the noise to the virtual MRI image, the virtual MRI image (complex number) is divided into first real number data and first imaginary number data and noises are added to the first real number data and the first imaginary number data and then the first real number data and the first imaginary number data are integrated again.

In the performing of the network learning, the virtual MRI image with the added noise is divided into second magnitude data and second phase data and the second magnitude data and the second phase data are input to the electrical conductivity reconstruction network to estimate an electrical conductivity for a kernel point from a kernel matrix of the second magnitude data and the second phase data.

In the performing of network learning, a label of the electrical conductivity reconstruction network is designated by a value corresponding to a center of a kernel matching in the same position based on the ground-truth electrical conductivity map.

In the performing of network learning, a bias is applied to the first magnitude data to generate dependency for a phase in every training process.

In the performing of network learning, the training is performed by differently updating a noise distribution which is reflected to the first magnitude data and the first phase data in every training process.

According to another aspect of the present embodiment, an electrical conductivity map reconstruction apparatus includes a processor and a storage medium storing a program executed by the processor. The processor is configured to divide a magnetic resonance imaging (MRI) for a biological tissue into first magnitude data and first phase data and generate an electrical conductivity map from the first magnitude data and the first phase data, by an electrical conductivity reconstruction network.

As described above, according to the exemplary embodiments of the present disclosure, an electrical conductivity map for high resolution clinical data with a low SNR is reconstructed by generating virtual magnetic resonance imaging data and ground-truth electrical conductivity map data based on simulated data and adding a noise to the virtual magnetic resonance imaging data to train a previously designed deep learning network.

Even if the effects are not explicitly mentioned here, the effects described in the following specification which are expected by the technical features of the present disclosure and their potential effects are handled as described in the specification of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a view illustrating an error according to a mathematical assumption in an EPT reconstruction method of the related art;

FIG. 2 is a view illustrating noise amplification in an EPT reconstruction method of the related art;

DETAILED DESCRIPTION OF THE EMBODIMENT

Hereinafter, in the description of the present disclosure, a detailed description of the related known functions will be omitted if it is determined that the gist of the present disclosure may be unnecessarily blurred as it is obvious to those skilled in the art and some exemplary embodiments of the present disclosure will be described in detail with reference to exemplary drawings.

Figure 3:
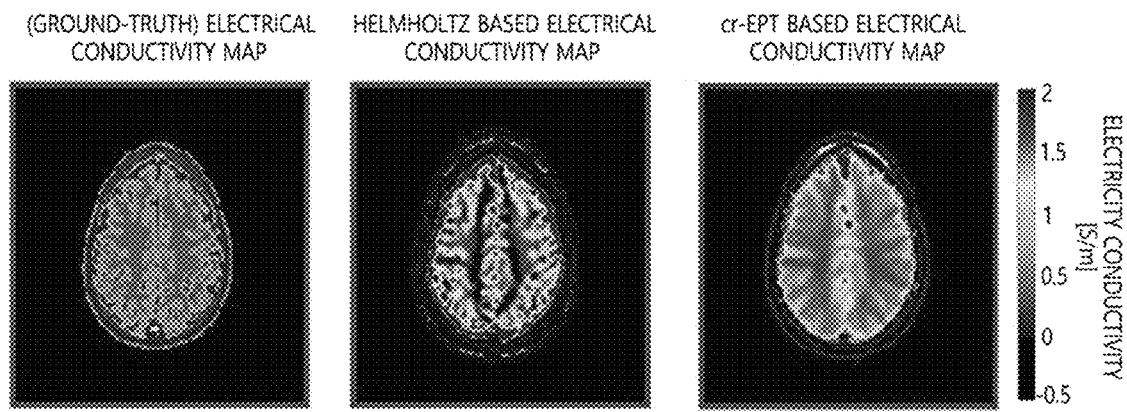
FIG. 3 is a view illustrating an error according to a mathematical assumption in an EPT reconstruction method which attempts for a mathematical overcome.
Figure 4:
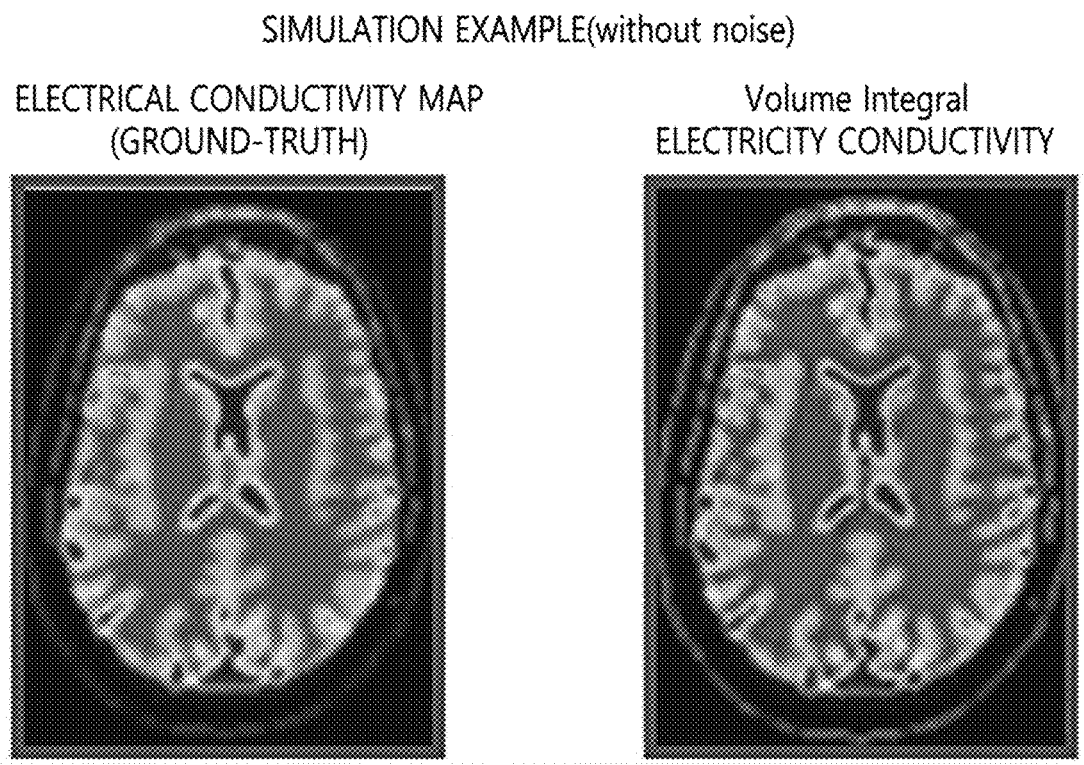
FIGS. 4 and 5 are views illustrating a problem of another EPT reconstruction method which attempts for a mathematical overcome.
Figure 5:
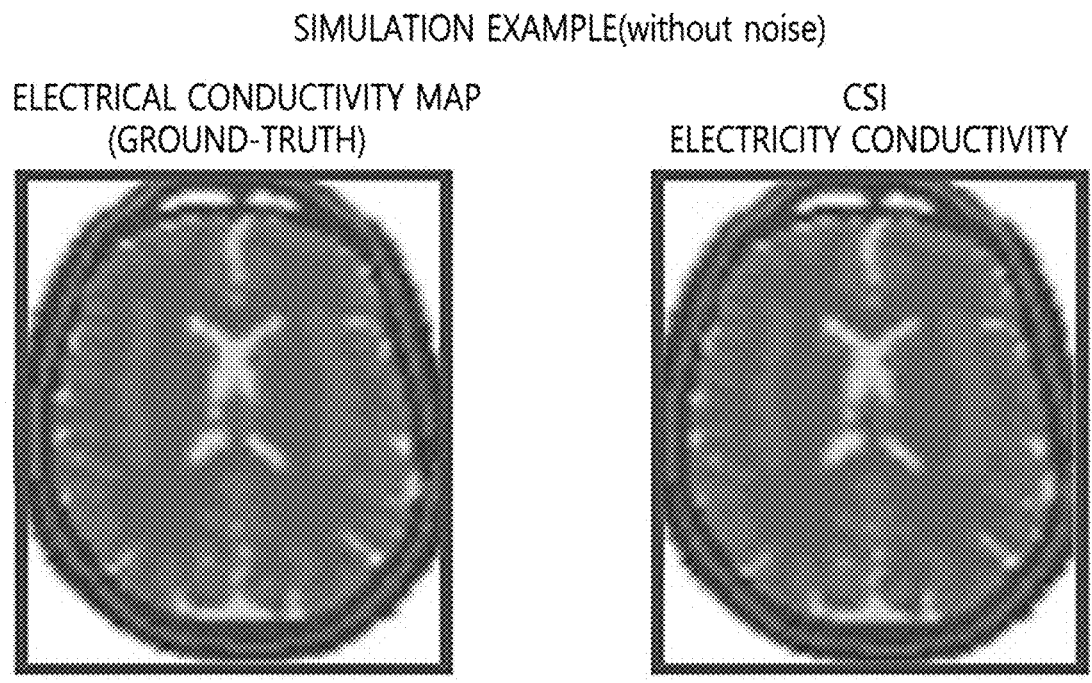

FIG. 1 is a view illustrating an error according to a mathematical assumption in an EPT reconstruction method of the related art, FIG. 2 is a view illustrating noise amplification in an EPT reconstruction method of the related art, FIG. 3 is a view illustrating an error according to a mathematical assumption in an EPT reconstruction method which attempts for a mathematical overcome, and FIGS. 4 and 5 are views illustrating a problem of another EPT reconstruction method which attempts for a mathematical overcome.

The electrical conductivity is one of electrical properties for the biological tissue, and for example, may be estimated by utilizing RF magnetic field information which is induced into the body from the MRI device. Here, the biological tissue includes various human organs as well as a human brain. The in-body electrical conductivity may be estimated using Maxwell Equation and Helmholtz equation induced by mathematical assumptions on a spin-echo based image which is utilized in the clinical environment. For example, a phase based electrical conductivity reconstruction method may be applied. The electrical conductivity for the human tissue is utilized as a quantitative biomarker for SAR measurement and pathological diagnosis by the MRI apparatus.

The Helmholtz equation is expressed by Equation 1.

$$-\nabla^2 H = \frac{\nabla \kappa}{\kappa} \times (\nabla \times H) + \omega^2 \mu \kappa H \qquad \text{[Equation 1]}$$

H is a magnetic field, k is σ+iwε, σ is a (electrical) conductivity, ε is a permittivity, w is an angular frequency, μ is a permeability, k is a complex permittivity, and the complex permittivity is expressed as a+bi in which "a" part indicates a real number and a "bi" part indicates an imaginary number.

From Equation 1, the truncated-Helmholtz equation (an equation for using the phase based electrical conductivity reconstruction) may be induced.

$$-\nabla^2 H = \frac{\nabla(\sigma + i\omega\varepsilon)}{\sigma + i\omega\varepsilon} \times (\nabla \times H) - i\omega\mu(\sigma + i\omega\varepsilon)H \qquad \text{[Equation 2]}$$

Piecewise constant assumption ($\nabla K \approx 0$): The electrical conductivity or permittivity in the body is not changed. However, actually, the electrical conductivity or permittivity is changed due to various body tissue compositions (for example, a cerebrospinal fluid, a white matter, a gray matter) so that the error occurs.

The phase based electrical conductivity reconstruction equation (Phase-based EPT) is expressed by Equations 3 and 4.

$$\sigma(r) + i\omega\varepsilon(r) \approx \frac{\nabla^2 H^+(r)}{i\omega\mu H^+(r)} \quad \text{[Equation 3]}$$

$$\sigma \approx \frac{\nabla^2 \varphi_\pm}{2\mu_0\omega} \quad \text{[Equation 4]}$$

Referring to FIG. 1, the Helmholtz equation includes numerous mathematical assumptions so that it shows a different result from the ground-truth.

There are some problems in the electrical conductivity map reconstruction process. Noise amplification, boundary artifacts, a limited practical image resolution, and difficulty in measuring ground-truth electrical conductivity are typical examples.

A spatial derivative "Laplacian operator" used for the reconstruction operation amplifies the noise during the reconstruction process to make it difficult to observe the resulting image. The Laplacian operator used during the electrical conductivity reconstruction process corresponds to a high pass filter from the point of view of image processing.

When the imaging resolution for an object is lowered or repeated imaging is performed from the point of view of the MRI hardware, a noise suppression effect of the acquired image may be expected. However, in an actual clinical environment, the object is a patient so that a high resolution imaging is requested for a limited time, which makes it difficult to utilize such approach.

Referring to FIG. 2, the MRI image inevitably includes the noise and a signal-to-noise ratio (SNR) of a spin-echo MRI image acquired in the clinical environment is approximately 20. It means that the lower the SNR, the more the noises are included.

In order to overcome the limitation of the electrical conductivity map reconstruction process, various efforts for improving the algorithm have been attempted. Representatively, a method of replacing a Laplacian operator with a magnitude N×N of the related art with a large size image filter to apply the image filter to an operation process has been proposed.

In order to solve the boundary artifact problem, partial differential equation-based algorithms which use segmentation information for a tissue in the MRI image or add a convection-response term have been proposed. However, there is a limit that a kernel size which is increased as much as the intensity of the noise to be suppressed deteriorates an actual resolution for the reconstructed electrical conductivity map.

As another reconstruction method, an integral based method for avoiding the direct operation of the differential operator has been proposed. As compared with the differential-based method, the performance for the noise amplification, the boundary artifact, the actual resolution lowering, and the ground-truth electrical conductivity map construction are significantly improved. However, during the operation process, not only prior information for a coil source is necessary, but also application to the phase-based electrical conductivity reconstruction algorithm is not possible so that it is still difficult to apply to the clinical environment.

Cr (convection-reaction)-EPT (convection-reaction phase-based electrical conductivity image) is expressed by Equation 5.

$$-c\nabla^2\rho + (\nabla\varphi^{tr} \cdot \nabla\rho) + \nabla^2\varphi^{tr}\rho - 2\omega\mu_0 = 0 \quad \text{[Equation 5]}$$

C is a diffusion coefficient, w is an angular frequency, $\rho$ is $1/\sigma$ (=1/electrical conductivity), $\rho$ is permeability, and $\varphi^{tr}$ is a phase.

Referring to FIG. 3, the convection-reaction phase-based electrical conductivity image is also different from the ground-truth map due to the mathematical assumption.

Referring to FIGS. 4 and 5, volume integral/CSI EPT (full-equation based electrical conductivity image may reconstruct a conductivity map close to the ground-truth map, but it is not possible to reconstruct only with the spin-echo MIR images. During the reconstruction process, a B1 size image and source information about the coil are necessary. That is, it is actually difficult to apply the algorithm to the actual clinical data.

In order to solve this problem, a deep learning network of reconstructing the electrical conductivity map from an MRI brain image is provided.

Figure 6:
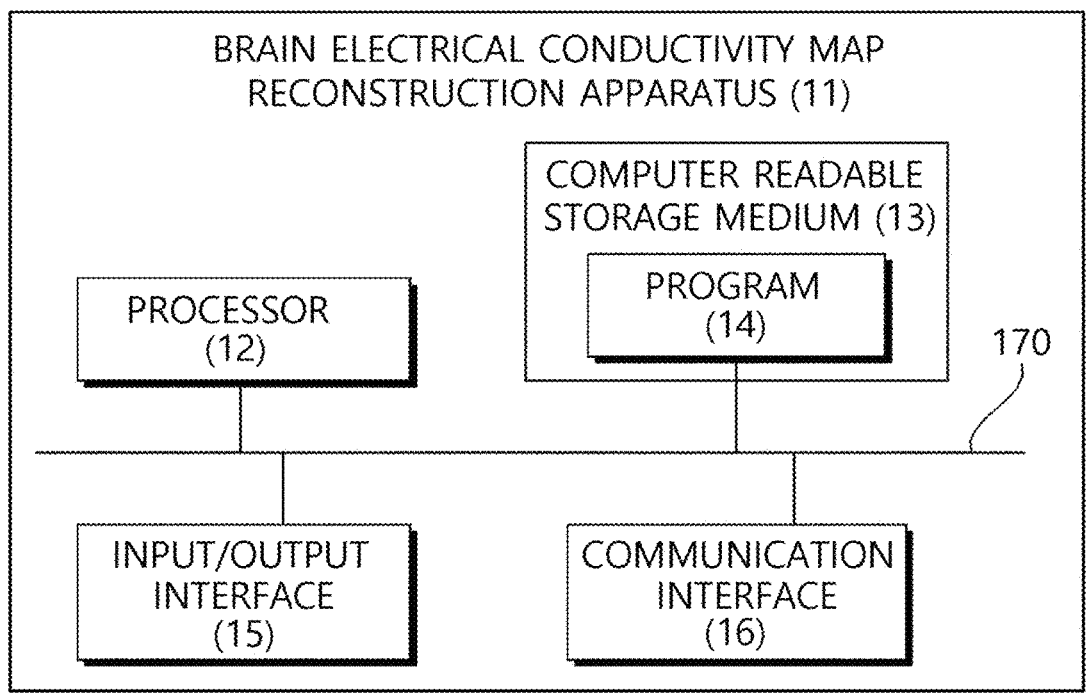
FIG. 6 is a view illustrating a brain electrical conductivity map reconstruction apparatus according to an exemplary embodiment of the present disclosure.

FIG. 6 is a view illustrating a brain electrical conductivity map reconstruction apparatus according to an exemplary embodiment of the present disclosure;

The brain electrical conductivity map reconstruction apparatus 11 includes at least one processor 120, a computer readable storage medium 13, and a communication bus 17.

The processor 120 controls the apparatus 11 to operate. For example, the processor 12 may execute one or more programs stored in the computer readable storage medium 130. One or more programs may include one or more computer executable instructions and the computer executable instruction may be configured to allow the apparatus 11 to perform the operations according to the exemplary embodiments when it is executed by the processor 12.

The computer readable storage medium 13 is configured to store a computer executable instruction or program code, program data and/or other appropriate format of information. A computer executable instruction or program code, program data and/or other appropriate type of information may also be provided by an input/output interface 15 or a communication interface 16. The program 13 stored in the computer readable storage medium 14 includes a set of instructions executable by the processor 12. In one exemplary embodiment, the computer readable storage medium 13 may be a memory (a volatile memory such as a random access memory, a non-volatile memory, or an appropriate combination thereof), one or more magnetic disk storage devices, optical disk storage devices, flash memory devices, and another format of storage mediums which is accessed by the brain electrical conductivity map reconstruction apparatus 11 and stores desired information, or an appropriate combination thereof.

The communication bus 17 interconnects various components of the brain electrical conductivity map reconstruction apparatus 11 including a processor 12 and a computer readable storage medium 13 to each other.

The apparatus 11 may include one or more input/output interfaces 15 and one or more communication interfaces 16 which provide an interface for one or more input/output devices. The input/output interface 15 and the communication interface 16 are connected to the communication bus 17. The input/output device (not illustrated) may be connected to the other components of the apparatus 11 by means of the input/output interface 15.

The processor 12 of the brain electrical conductivity map reconstruction apparatus 11 divides the magnetic resonance imaging (MRI) into first magnitude data and first phase data and generates a brain electrical conductivity map from the first magnitude data and the first phase data by means of the electrical conductivity reconstruction network.

The electrical conductivity reconstruction network is trained through a process of composing a virtual MRI image without a noise based on simulated data, generating the ground-truth electrical conductivity map based on the simulated data, adding the noise to the virtual MRI image, and performing the network learning using the virtual MRI image with the noise and the ground-truth electrical conductivity map.

The simulated data is formed by configuring a simulation environment using a simulation human phantom and a radio frequency (RF) coil and acquiring data without having a noise about an RF magnetic field, a current density, and an electrical field.

The virtual MRI image without having a noise is acquired by means of a relational expression including a repeated time TR and an echo time TE required to set the RF magnetic field and a contrast and a first relaxation time T1 and a second relaxation time T2 required to produce MR contrast (e.g., T2-w image) for each human brain region.

The ground-truth electrical conductivity map is acquired by a relational expression including a current density and an electrical field.

The electrical conductivity reconstruction network applies a virtual MRI image with a noise added by processes of dividing the virtual MRI image into first real number data and first imaginary number data and adding and integrating noises to the first real number data and the first imaginary number data.

The electrical conductivity reconstruction network divides the virtual MRI image with the added noise into second magnitude data and second phase data and inputs the second magnitude data and the second phase data to the electrical conductivity reconstruction network to estimate the electrical conductivity for the kernel point from a kernel matrix of the second magnitude data and the second phase data.

The electrical conductivity reconstruction network designates a label of the electrical conductivity reconstruction network by a value corresponding to a center of a kernel matching the same position based on the ground-truth electrical conductivity map.

The electrical conductivity reconstruction network generates the dependency for the phase by applying a bias to the first magnitude data in every training process. The electrical conductivity reconstruction network is trained by differently updating a noise distribution which is reflected to the second magnitude data and the second phase data for every training process.

Figure 7:
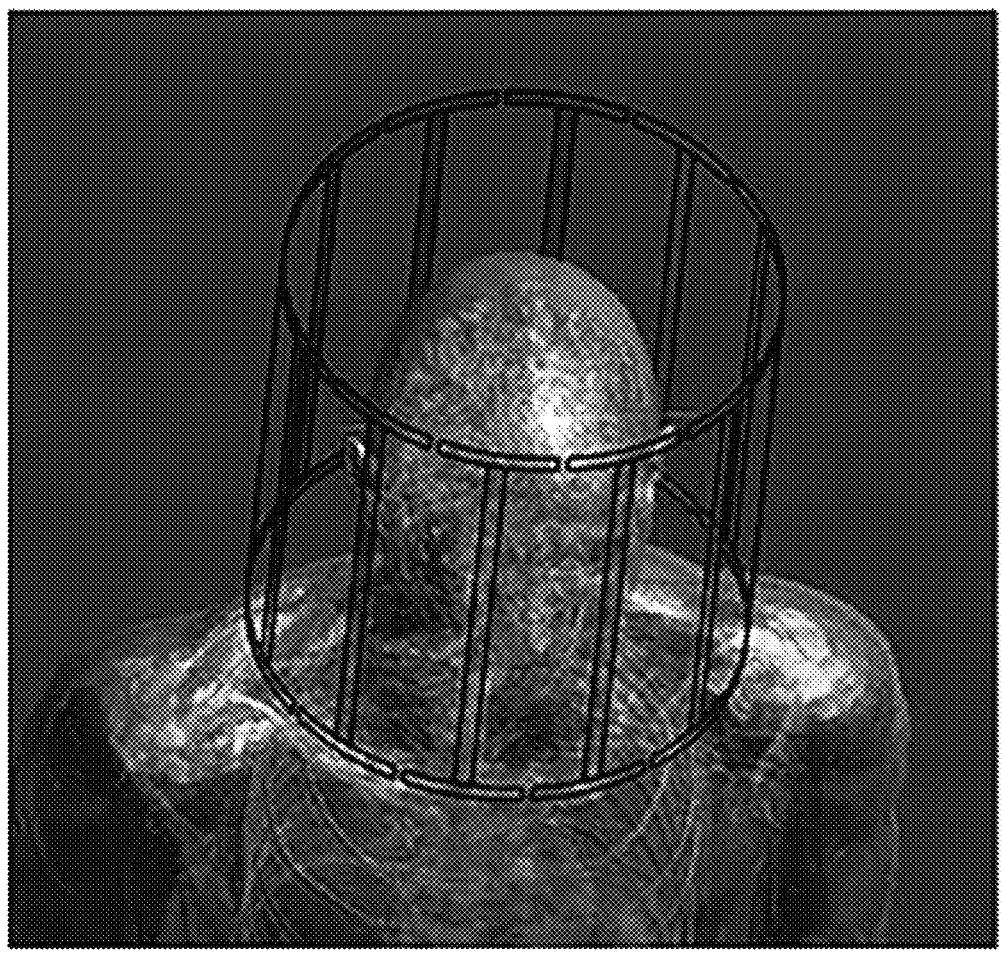
FIG. 7 is a view illustrating a simulation environment of a brain electrical conductivity map reconstruction apparatus according to an exemplary embodiment of the present disclosure.
Figure 8:
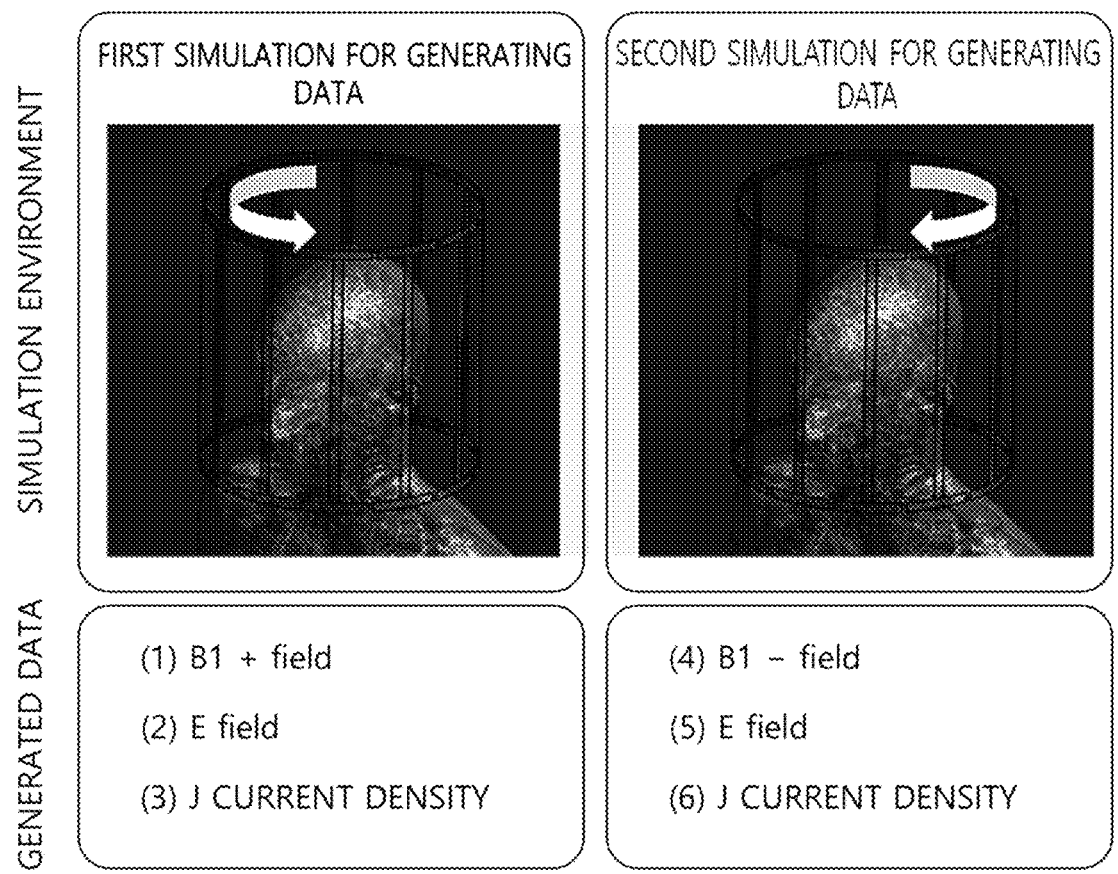
FIGS. 8 to 10 are views illustrating simulated data of a brain electrical conductivity map reconstruction apparatus according to an exemplary embodiment of the present disclosure.
Figure 9:
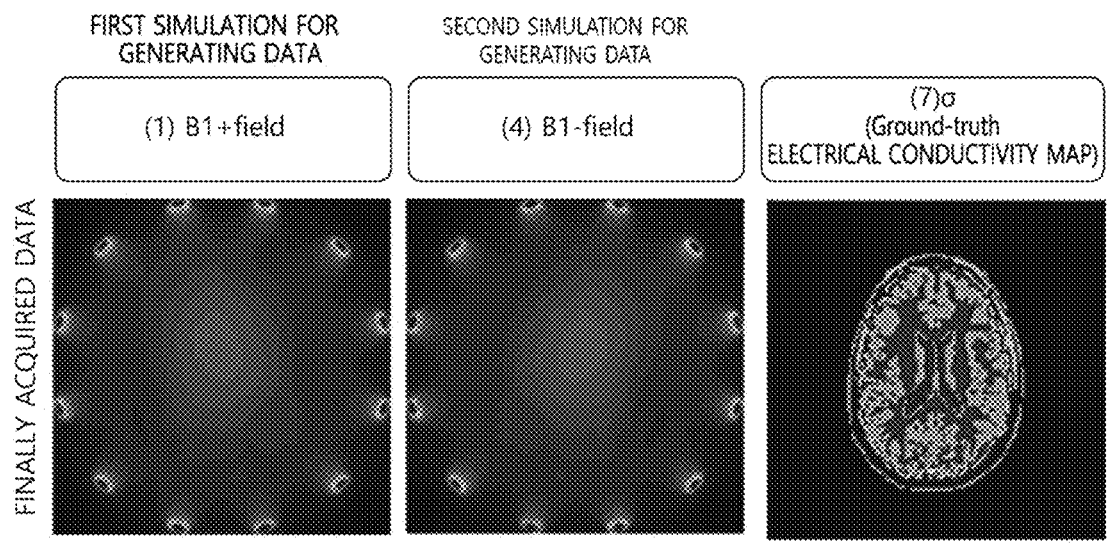
Figure 10:
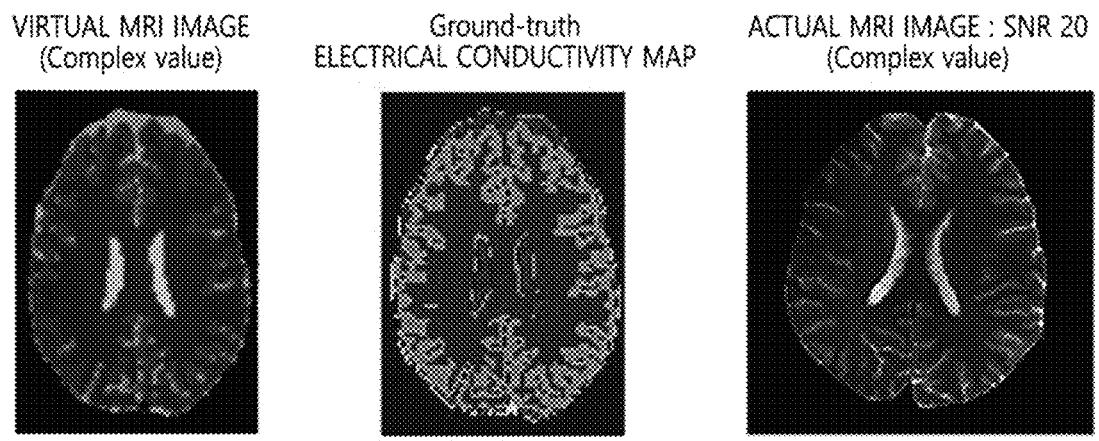

FIG. 7 is a view illustrating a simulation environment of a brain electrical conductivity map reconstruction apparatus according to an exemplary embodiment of the present disclosure and FIGS. 8 to 10 are views illustrating simulated data of a brain electrical conductivity map reconstruction apparatus according to an exemplary embodiment of the present disclosure.

The MRI image acquired for the clinical purpose may include a high intensity (low SNR of an image) of a noise which causes a distortion of a reconstruction image during the electrical conductivity reconstruction process so that it is important to minimize the influence thereof.

The mathematical reconstruction algorithm of the related art may have a limitation that it is difficult to reconstruct the in-vivo ground-truth electrical conductivity map from a spin-echo based image.

In the present disclosure, an in-brain ground-truth electrical conductivity map is reconstructed from the spin-echo MRI image by utilizing the RF magnetic field data and the deep learning network generated by the finite difference time domain (FDTD) simulation.

In order to generate data for training deep learning, an actual 3T MRI environment is simulated by utilizing finite-difference time-domain (FDTD) simulation software and a human head phantom and data without having a noise of an RF magnetic field B1, a current density J, and an electric field E is generated. An electrical physical value for a human organ is set in advance to the simulation human phantom. A current frequency of a simulation coil is set to 128 MHz so that the RF coil resonates at 3 T (the unit of magnetic field), like the real clinical MRI.

Virtual spin-echo MRI image data and a corresponding ground-truth electrical conductivity map are composed based on the simulated data. The deep learning network suitable for the training purpose is developed based on the composed training data set. The deep learning network is trained by adding an arbitrary noise and a bias according to the noise intensity in the actual MRI image to the training data set in every training process.

It is practically difficult to obtain the ground-truth electrical conductivity information without a bias due to the mathematical assumption from the human body.

According to the present disclosure, network training data which utilizes the RF simulation is generated. Data that simulates the actual spin-echo MRI image and the ground-truth electrical conductivity data are generated by utilizing the simulation and used for the network training. In order to simulate the 3T MRI, the simulation environment configures a birdcage RF coil which resonates at 128 MHz and places the head phantom therein to generate data without the noise of B1+, B1−, the current density, and the electrical field. A final image parameter of the data is set to have a resolution of 1.0×1.0 mm$^2$ and a thickness of 2 mm. The virtual spin-echo MRI image without a noise and the ground-truth electrical conductivity map are composed based on the generated data and are expressed by Equation 6 (ground-truth electrical conductivity a) and Equation 7 (virtual MRI image S).

$$\sigma = J/E \quad \text{[Equation 6]}$$

Referring to FIGS. 8 and 9, the simulation for generating data is performed by setting a rotation direction of the current in the coil in a counterclockwise direction or a rotation direction of the current in the coil in a clockwise direction. Information to be finally obtained is an electrical conductivity map so that it is not necessary to consider the direction of the field in the calculation.

$$\text{Approximated MRI Image} = V_1 \cdot M_0(r) \cdot \left(1 - \exp\left(-\frac{TR}{T_1}\right)\right) \cdot \quad \text{[Equation 7]}$$
$$\exp\left(-\frac{TE}{T_2}\right) \cdot H^-(r) \cdot \exp(i\phi^+(r)) \cdot \sin(V_2 \alpha |H^+(r)|)$$

$V_1$ and $V_2$ are scaling factors determined by an MRI machine.

A is a rotation amount experienced by magnetization (M) while applying the RF pulse in the MRI device and has information from clinical data.

$M_0(r)$ has the largest magnetized value $M_0$ in the tissue before the MRI scan process. TR/TE is a value set to create a contrast of the MRI image and has information from the clinical data.

$H^+$ is a magnetic field component which rotates in the same direction as a direction of nuclear precession, $H^-$ is a magnetic field component which rotates in an opposite direction to the direction of nuclear precession, $H^-=abs(H^-) \cdot exp(i.angle(H^-))$, $\Phi^+=angle(H^+)$, $|H^+|=abs(H^+)$.

T1 and T2 have different values for every brain part of the human and have generally known values for every part.

That is, only when information for distinguishing a human body region for simulated data is provided, the composing is possible. Referring to FIG. 10, finally, the MRI image is composed with reference to the clinical data.

According to the present disclosure, an artificial neural network (ANN) for reconstructing the ground-truth electrical conductivity is designed.

In the deep learning based electrical conductivity reconfiguration methods proposed in the related art, a label image kernel size to be reconstructed is fixed to be the same as the input (image-to-image estimation). This approach may not only require a high computational load of the network by forcing the reconstruction performance for the entire output kernel, but also lead to the deterioration of the generalization performance for actually applying the MRI data.

Figure 11:
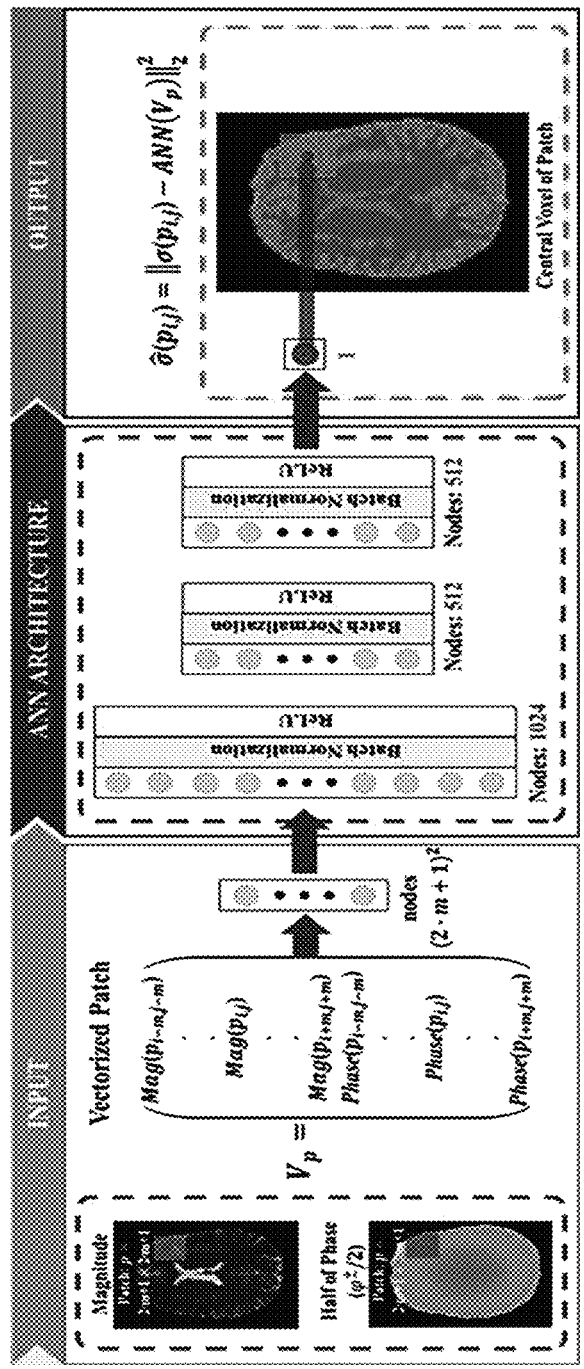
FIG. 11 is a view illustrating an electrical conductivity reconstruction network of a brain electrical conductivity map reconstruction apparatus according to an exemplary embodiment of the present disclosure.
Figure 12:
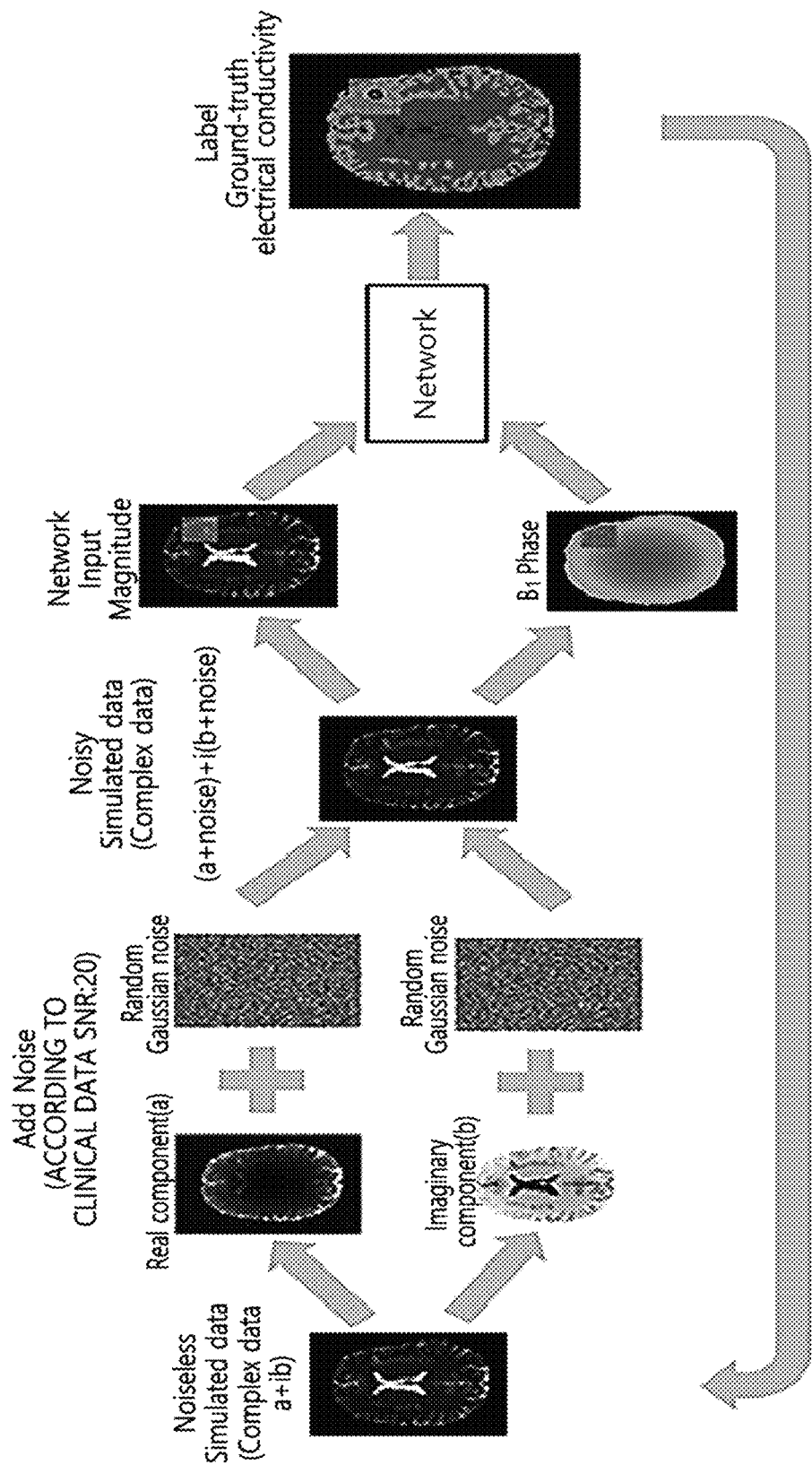
FIG. 12 is a view illustrating network learning of a brain electrical conductivity map reconstruction apparatus according to an exemplary embodiment of the present disclosure.

FIG. 11 is a view illustrating an electrical conductivity reconstruction network of a brain electrical conductivity map reconstruction apparatus according to an exemplary embodiment of the present disclosure and FIG. 12 is a view illustrating network learning of a brain electrical conductivity map reconstruction apparatus according to an exemplary embodiment of the present disclosure.

The deep learning network artificial neural network (ANN) shows not only a good efficiency for treating the ill-conditioned problem in the medical image processing, but also the robustness of the model against the noise and outliers.

According to the present exemplary embodiment, it is implemented to estimate the electrical conductivity of the kernel center from a patched image kernel (image-to-point estimation) by utilizing the ANN network. The network is configured with three hidden layers including batch normalization and ReLU activation functions and number of neurons of the layers are 1024, 512, and 512, respectively. The entire process will be illustrated in FIG. 12.

The simulated data is used for the network training by the following processes. The used MRI image is formed of a complex value (a+bi).

First, simulated data used for the proposed network input is patched with 11×11 kernel (in which stride is 1) and a label of the network is designated by a value corresponding to a center of the kernel located in the same position as the input from the ground-truth electrical conductivity map.

Second, in order to generate the dependency on the phase during the network training process, a bias is applied to the magnitude information of the input in every epoch.

Third, in order to train the robustness of the network model against the noise, a noise distribution (a noise strength: SNR=20 to 40) is updated be added to the input data in every epoch.

Finally, the input data in which the bias and the noise are updated is divided into magnitude and phase information and then vectorized to be used for the network and is expressed by Equation 8.

$$\text{Input} = \begin{pmatrix} \text{Magnitude (pixel}_1) \\ \vdots \\ \text{Magnitude (pixel}_n) \\ \text{Phase (pixel}_{n+1}) \\ \vdots \\ \text{Phase (pixel}_{2n}) \end{pmatrix} \text{ where}$$ [Equation 8]

Manitude = $|S_{kernel}|$, Phase = $\angle S_{kernel}$

During the training process, the network is optimized by utilizing Adam optimization having a learning rate of 0.0001 and a batch size is set to 64, and an epoch is set to 200.

Figure 13:
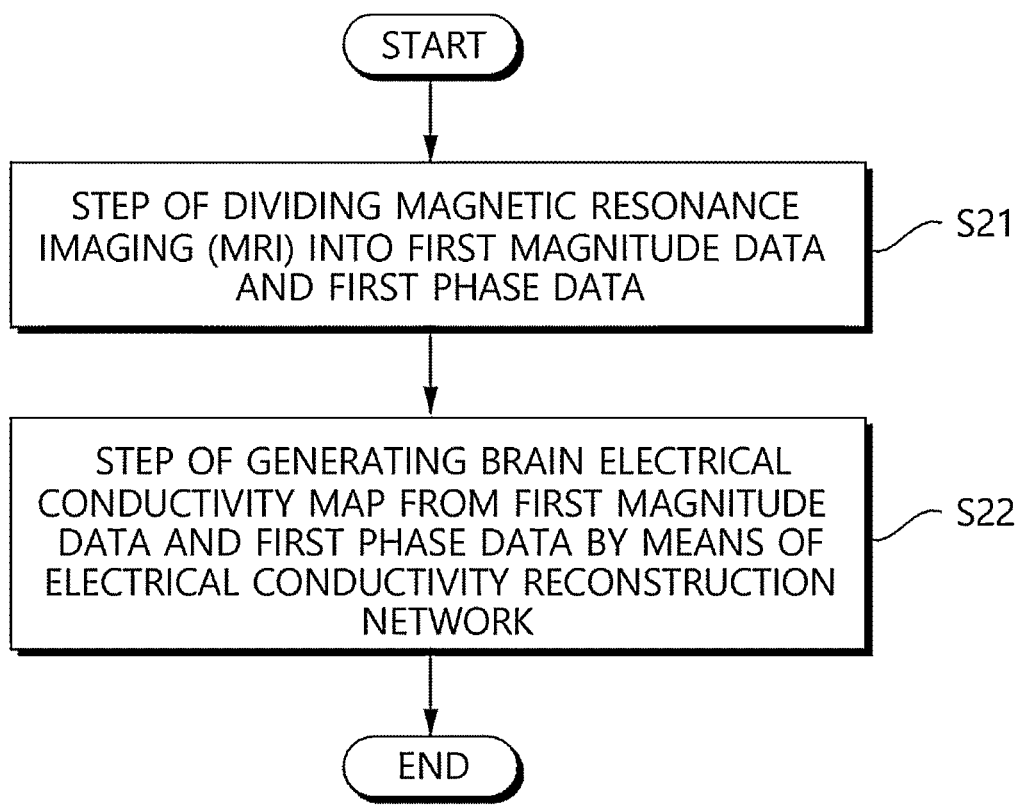
FIGS. 13 and 14 are views illustrating a brain electrical conductivity map reconstruction method according to another exemplary embodiment of the present disclosure.
Figure 14:
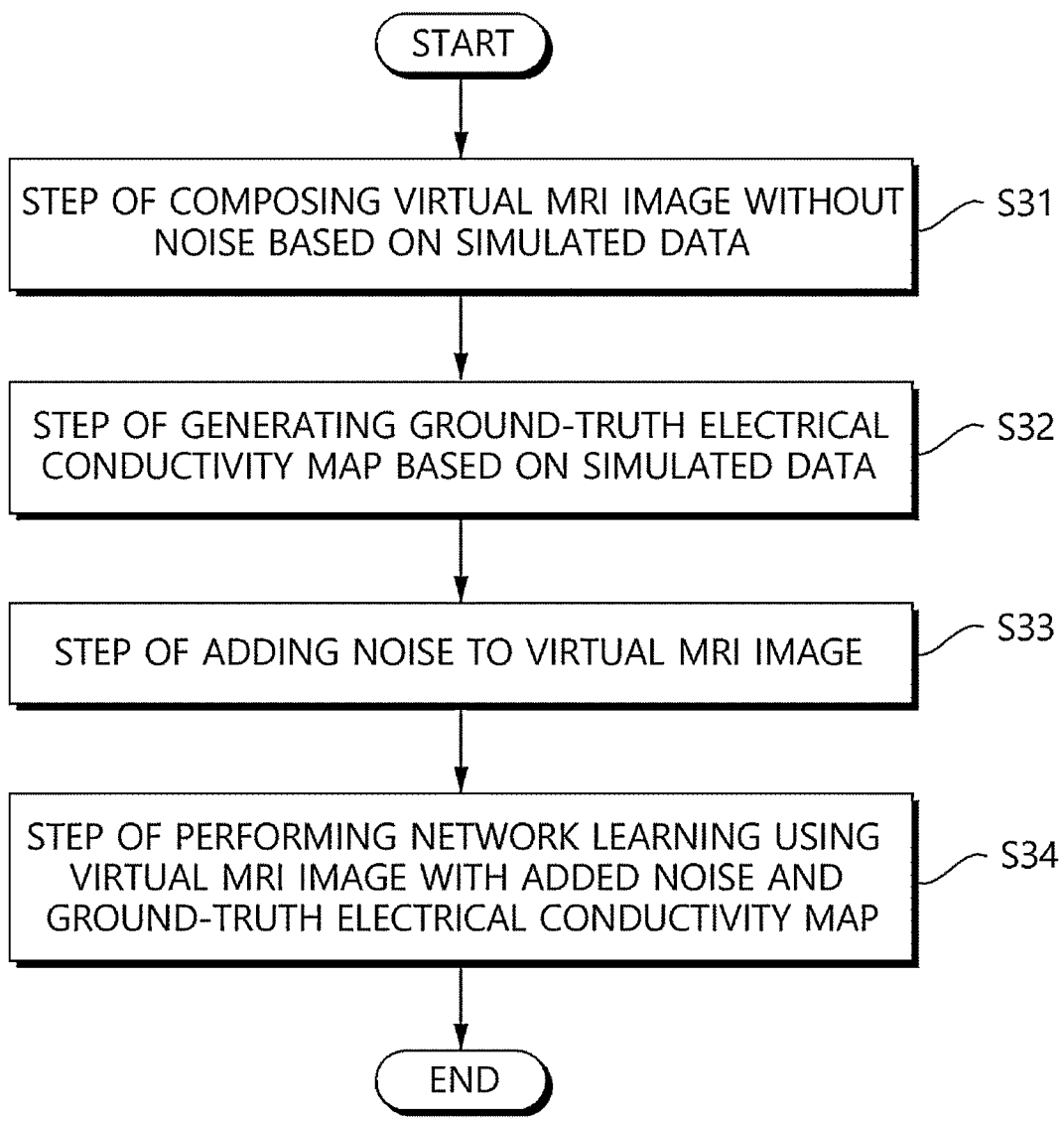

FIGS. 13 and 14 are views illustrating a brain electrical conductivity map reconstruction method according to another exemplary embodiment of the present disclosure.

The brain electrical conductivity map reconstruction method includes a step S21 of dividing the magnetic resonance imaging (MRI) into first magnitude data and first phase data and a step S22 of generating a brain electrical conductivity map from the first magnitude data and the first phase data by means of the electrical conductivity reconstruction network.

The electrical conductivity reconstruction network is trained through a step S31 of composing a virtual MRI image without a noise based on simulated data, a step S32 of generating the ground-truth electrical conductivity map based on the simulated data, a step S33 of adding the noise to the virtual MRI image, and a step S34 of performing the network learning using the virtual MRI image with the noise and the ground-truth electrical conductivity map.

The simulated data is formed by configuring a simulation environment using a simulation human body phantom and a radio frequency (RF) coil and acquiring data without having a noise about an RF magnetic field, a current density, and an electrical field.

The virtual MRI image without having a noise is acquired by means of a relational expression including a repeated time TR and an echo time TE required to set the RF magnetic field and a contrast and a first relaxation time T1 and a second relaxation time T2 required to produce MR contrast (e.g., T2-w image) for each human brain region.

The ground-truth electrical conductivity map is acquired by a relational equation (Equation 6) including the current density and the electrical field.

In the step S33 of adding the noise to the virtual MRI image, the virtual MRI image is divided into first real number data and first imaginary number data and noises are added to the first real number data and the first imaginary number data and then the first real number data and the first imaginary number data are integrated again.

In the step S34 of performing the network learning, the virtual MRI image with the added noise is divided into second magnitude data and second phase data and the second magnitude data and the second phase data are input to the electrical conductivity reconstruction network to estimate the electrical conductivity for the kernel point from a kernel matrix of the second magnitude data and the second phase data.

In the step S34 of performing the network learning, the label of the electrical conductivity reconstruction network is designated by a value corresponding to the center of the kernel matching the same position based on the ground-truth electrical conductivity map.

In the step S34 of performing the network learning, a bias is applied to the first magnitude data in every training process to generate the dependency on the phase.

In the step S34 of performing the network learning, the training is performed by updating different noise distribution which is reflected to the second magnitude data and the second phase data for every training process.

Figure 15:
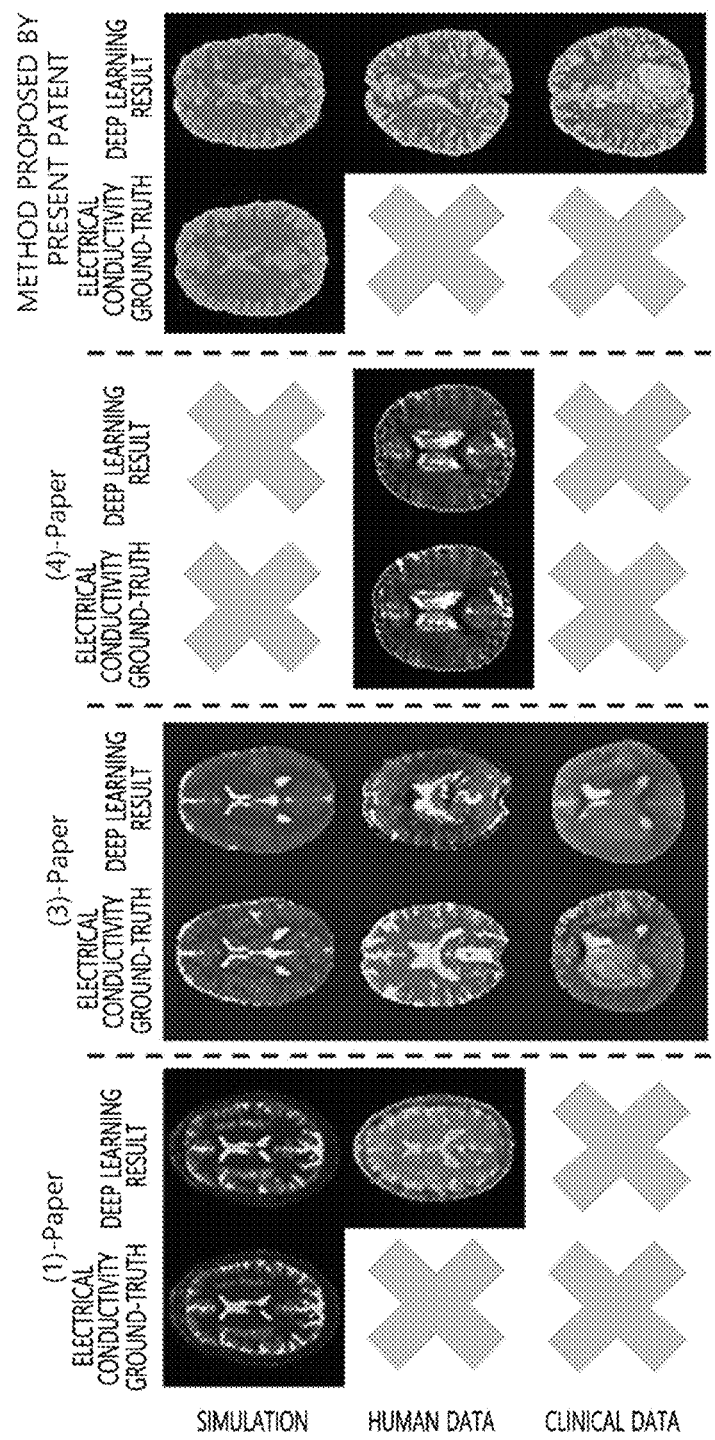
FIGS. 15 to 17 are views illustrating a result of performing simulations and in-vivo datasets (healthy volunteer and meningioma patient) according to exemplary embodiments of the present disclosure.
Figure 16:
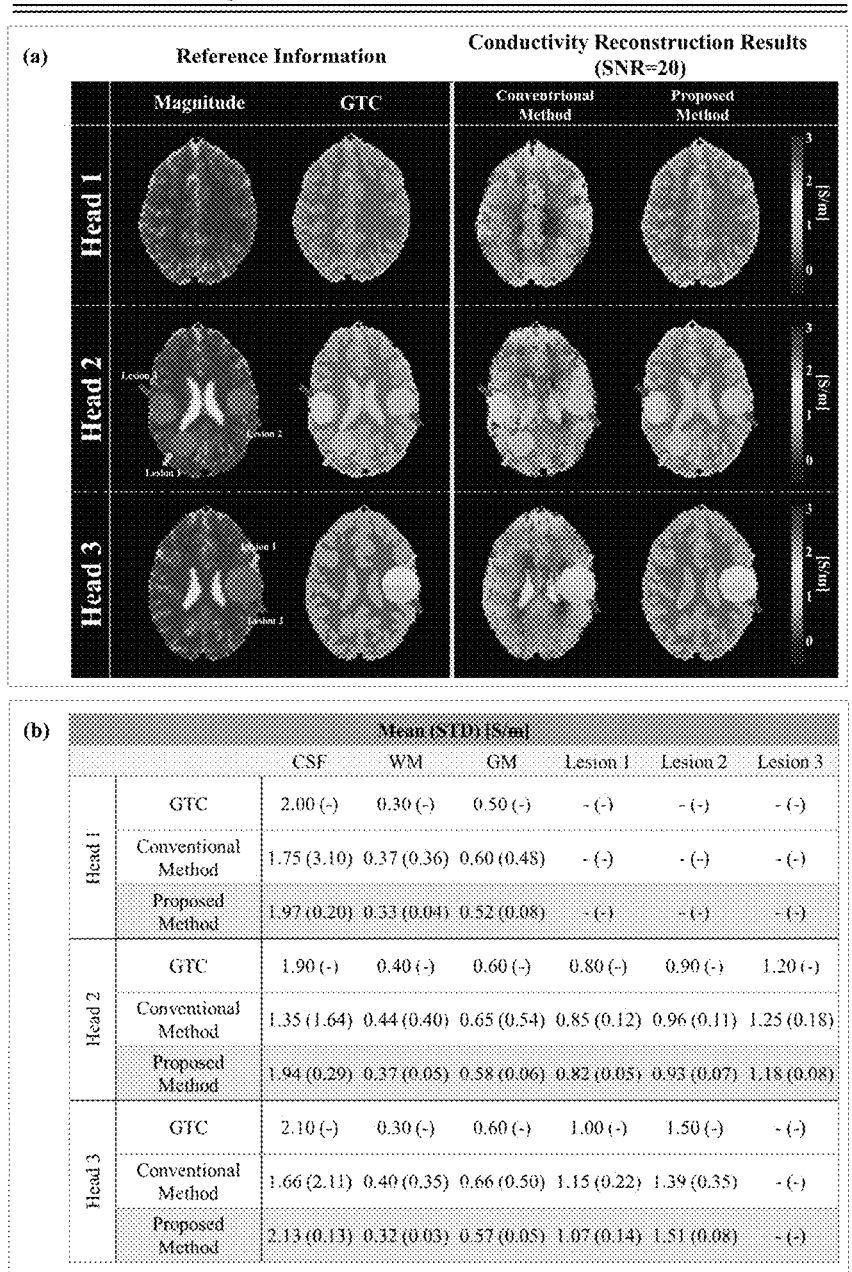
Figure 17:
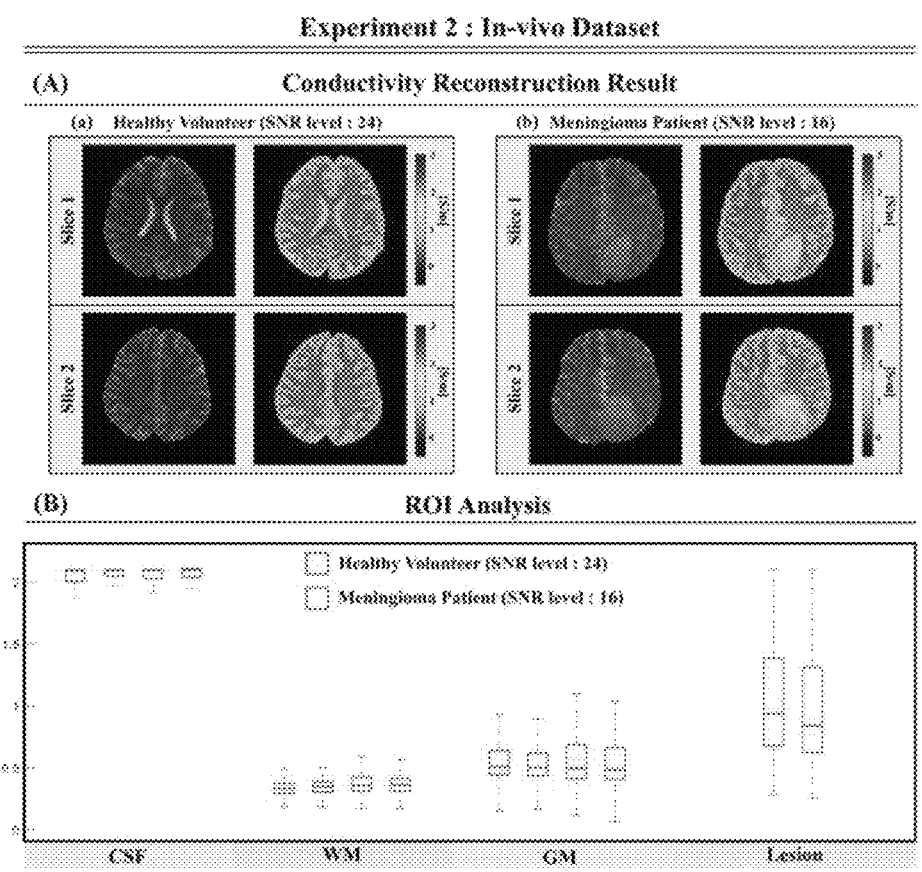

FIGS. 15 to 17 are views illustrating a result of performing simulations and in-vivo datasets (healthy volunteer and meningioma patient) according to exemplary embodiments of the present disclosure.

Referring to FIG. 5, it is confirmed that in non-patent document 1, a full equation based algorithm was used, a network was CNN, a network input & output size was 2D slice whole brain image, training data was a simulated data set, label data was a ground-truth electrical conductivity map, a data resolution was 2×2 mm$^2$, a simulated data SNR for test was 100 (successful), and the human data test was applicable, and the clinical data test was not performed.

It is confirmed that in non-patent document 2, the deep learning configuration was the same as non-patent document 1 (full equation based), a simulated data SNR for test was 100 (successful), and human and clinical data tests were not performed.

It is confirmed that in non-patent document 3, phase-based electrical conductivity reconstruction algorithm was used, the network was a patch based CNN, training data was simulation and human data sets, label data (simulation: ground-truth electrical conductivity map+human: phase based electrical conductivity map reconfigured by utilizing human tissue information and a bilateral denosing median filter), a data resolution was 2×2 mm$^2$, the ground-truth of the human data used for the training data used only data which was appropriately processed to be reconfigured, a simulated data SNR for test was 100 (but as the result, the performance was lower than those in non-patent documents 1 and 2), application of the human data test failed (deteriorated performance), and the application of the clinical data test failed (deteriorated performance).

It is confirmed that in non-patent document 4, a phase-based electrical conductivity reconstruction algorithm was used, the network was a patch based ANN, the network input & output size was 2D patch matrix of 9×9, training data was a human data set, label data was a cr_EPT reconstruction electrical conductivity map, a data resolution was 1.875×1.875 mm$^2$, label data of human data used for training data utilized only data which was appropriately processed to be reconstructed, a simulated data SNR for test needed to be high (at least 100) as estimated from data acquisition information, a human data test was applicable, but was different from the ground-truth electrical conductivity map due to the use of the cr_EPT result in the label, and the clinical data test was not performed.

According to the present exemplary embodiment, a phase based electrical conductivity reconstruction algorithm was used, the network was a patch based ANN, a network input size was a 2D patch matrix of 11×11, a network output size was 2D patch matrix of 1×1, training data was simulated data set, label data was a ground-truth electrical conductivity map, a data resolution was 1×1 mm$^2$, a simulated data SNR for test was 20, the human data test was applicable, and clinical data test was applicable.

In order to evaluate the deep learning model trained with an experiment data set, simulated data and MRI brain data of the hospital were utilized and a total of three types of data were used for the task, including 1) spin-echo simulated data which is not included in the network training, 2) a spin-echo MRI image for healthy volunteer, and 3) a spin-echo MRI image for meningioma patient captured in an actual clinical environment.

1) The data was composed by referring to the actual MRI data and the scan parameter (2) and (3), and the image composing parameter was TR/TE (=4500/80 [ms]), an image resolution was 1.0×1.0 [mm$^2$], a number of slices was 20, and a thickness was 2 [mm].

The MRI scan parameter of the image (2) was 2D, TR/TE was 4500/80 [ms], an image resolution was 1.0×1.0 [mm$^2$], a number of slices was 20, and a thickness was 3 [mm]. The MRI scan parameter of the image (3) was 2D, TR/TE was 4363/95 [ms], a resolution was 0.625×0.75 [mm$^2$], a number of slices was 100, and a thickness was 2 [mm].

(3) The image resolution of the experimental data was reconstructed to 1.0×1.0 (mm$^2$) to be adjusted to the image parameter used for the network training to be utilized for the experiment.

It is actually difficult to obtain the ground-truth electrical conductivity information for the acquired body data. Accordingly, for the quantitative evaluation, simulated data in which the ground-truth electrical conductivity information is permitted is utilized to estimate an electrical conductivity value (mean/std) for each phantom ROI (cerebrospinal fluid, white matter, and gray matter regions) to be compared with the ground truth. Further, in experiments (2) and (3), the algorithm was applied to the actual MRI image and the ROI analysis result was compared with literature value.

(1) First Experiment: Simulated Data which Simulates Actual Spin-Echo MRI Image

In this experiment, simulated data which was not included in the network training was utilized to investigate a network performance. An algorithm result was as illustrated in FIG. 16A. Three simulated data used for the test was configured by four regions including a cerebrospinal fluid, a white matter, a gray matter, and a lesion and the electrical conductivity was as follows: Cerebrospinal fluid: 2.00 (Head 1), 1.90 (Head 2), 2.10 (Head 3), White matter: 0.30 (Head 1), 0.40 (Head 2), 0.30 (Head 3), Gray matter: 0.50 (Head 1), 0.60 (Head 2), 0.60 (Head 3), and Lesions: None (Head 1), 0.80 (Head 2), 0.90 (Head 2), 1.20 (Head 3), 1.00 (Head 3), 1.50 (Head 3) [S/m] As an algorithm result, a mean (standard deviation) electrical conductivity for every region is as follows: Head 1: 1.97 (0.20), 0.33 (0.04), 0.52 (0.08), Head 2: 1.94 (0.29), 0.37 (0.05), 0.58 (0.06), 0.82 (0.05), 0.93 (0.07), 1.18 (0.08), and Head 3: 2.13 (0.13), 0.32 (0.03), 0.57 (0.05), 1.07 (0.14), 1.51 (0.08) [S/m] (see FIG. 16B). In contrast, the electrical conductivity value calculated by the Helmholtz phase based reconstruction algorithm is as follows: Head 1: 1.75 (3.10), 0.37 (0.36), 0.60 (0.48), Head 2: 1.35 (1.64), 0.44 (0.40), 0.65 (0.54), 0.85 (0.12), 0.96 (0.11), 1.25 (0.18), Head 3: 1.66 (2.11), 0.40 (0.35), 0.66 (0.50), 1.15 (0.22), 1.39 (0.35) [S/m]. This shows a stability of the proposed algorithm result.

(2) Second Experiment: MRI Image for Healthy Volunteer

In the second experiment, a generalization performance of the trained network for the MRI image of the healthy volunteer was investigated. The algorithm results were the same as those shown in FIG. 17 (A-a) and did not include a large bias when observed qualitatively. The algorithm results showed a mean (standard deviation) electrical conductivity of 1.94 (0.37), 0.36 (0.087), 0.61 (0.30) [S/m] for individual regions (the cerebrospinal fluid, the white matter, and the gray matter) and the distribution was the boxplot B for healthy volunteer of FIG. 17. The electrical conductivity values known from the literature were 1.65 to 2.14, 0.30 to 0.43, and 0.59 to 0.63 [S/m] for the cerebrospinal fluid, the white matter, and the gray matter, respectively. Accordingly, the deep learning network trained only with the simulated data predicted the electrical conductivity value within a reasonable range for the actual human MRI data.

(3) Third Experiment: MRI Image for Patient

Finally, the generalization performance of the trained network for a patient MRI image having a meningioma lesion was investigated. The algorithm results were the same as those shown in FIG. 17A-b. (2) As compared with the experimental result, it seemed to be more affected by the noise, but a large bias was not observed. The algorithm results showed a means (standard deviation) electrical conductivity of 1.90 (0.44), 0.39 (0.16), 0.64 (0.42) [S/m] for individual regions (the cerebrospinal fluid, the white matter, and the gray matter) and the distribution was the boxplot B for meningioma patient of FIG. 17. Additionally, the electrical conductivity for the meningioma lesion ROI was measured and compared with the literature value. The proposed algorithm measured the mean (standard deviation) electrical conductivity value of 0.96 (0.47) [S/m] for the entire lesion region and the electrical conductivity value for the lesion estimated by the literature was 0.83 (0.49). There is a difficulty in the quantitative analysis for the patient data due to the difficulty of the measurement of the in-vivo ground-truth electrical conductivity. However, the proposed algorithm network distinguished the lesion in the brain and represented an approximate value to a value estimated from the literature.

Since introduction of the EPT technique, numerous attempts have been made to improve the electrical conductivity reconstruction algorithm to solve the limitations. However, the phase based EPT algorithm result proposed in the related art includes mathematical assumptions and a bias generated by the noise of data so that it is different from the ground-truth electrical conductivity map. Some integral algorithms showed significant performance for the ground-truth electrical conductivity map reconstruction, but had difficulty to apply to the clinical environment due to the limitations such as prior information about a coil source required during the operation process, a long computational time, and difficulty to apply to the phase based electrical conductivity reconstruction algorithm.

Recently, even though the deep learning algorithms are receiving a lot of attentions in the EPT field, only one method has been proposed to reconstruct the deep learning based ground-truth electrical conductivity map from phase based information. The existing algorithm has several limitations, but the present disclosure overcomes the limitations.

First, the existing algorithm lacks the robustness of the model against the noise. The existing model considers the robustness of the data against the noise only for the SNR=100. A clinical data noise level utilized for the experiment in the present disclosure was SNR=20. Accordingly, it is difficult for the deep learning based reconstruction method proposed in the related art to be applied to some clinical environments which require a high resolution image and a limited imaging time. In contrast, according to the present disclosure, the electrical conductivity may be reconstructed even with data of lower SNR than that tested in the deep learning method of the related art without causing any problems.

Second, the existing algorithm limits the image resolution. The existing deep learning method was proposed to apply data with a resolution of 1.875×1.875 and 2.0×2.0 [mm$^2$]. In terms of acquisition of the MRI image, when the image resolution is lowered, the SNR of the image is increased, but the detail of the structure which is observable from the reconstructed electrical conductivity map is deteriorated. In contrast, according to the present disclosure, data with a resolution of 1.0×1.0 [mm$^2$] was applied so that the electrical conductivity map with a much higher resolution than that of the existing deep learning method may be observed.

Third, the existing algorithm shows a low generalization performance of the deep learning network. Even in the deep learning method proposed in the related art, the MRI images for the healthy volunteer and the patient were experimented, but were not successful. However, the present disclosure shows that in the in-vivo data experiment, the electrical conductivity may be reconstructed without having a large bias.

In an actual clinical environment, high-resolution imaging is required for the patient within a limited time so that it is difficult to provide the image acquisition environment for the EPT reconstruction. Because this imposes a low SNR on the taken MRI image, it makes it difficult for clinical observation for the feasibility study of pathology diagnosis with the existing algorithm alone, and additional measures are required to increase the SNR of the image to overcome the limitation.

When the method proposed by the present disclosure is used, it is possible to overcome the inefficiency and contribute to the feasibility study for the electrical conductivity image.

The apparatus may be implemented in a logic circuit by hardware, firm ware, software, or a combination thereof or may be implemented using a general purpose or special purpose computer. The apparatus may be implemented using hardwired device, field programmable gate array (FPGA) or application specific integrated circuit (ASIC). Further, the apparatus may be implemented by a system on chip (SoC) including one or more processors and a controller.

The apparatus may be mounted in a computing device or a server provided with a hardware element as a software, a hardware, or a combination thereof. The computing device or server may refer to various devices including all or some of a communication device for communicating with various devices and wired/wireless communication networks such as a communication modem, a memory which stores data for executing programs, and a microprocessor which executes programs to perform operations and commands.

In FIGS. 13 and 14, the respective processes are sequentially performed, but this is merely illustrative and those skilled in the art may apply various modifications and changes by changing the order illustrated in FIGS. 13 and 14 or performing one or more processes in parallel or adding another process without departing from the essential gist of the exemplary embodiment of the present disclosure.

The operation according to the exemplary embodiment of the present disclosure may be implemented as a program instruction which may be executed by various computers to be recorded in a computer readable medium. The computer readable medium indicates an arbitrary medium which participates to provide a command to a processor for execution. The computer readable medium may include solely a program command, a data file, and a data structure or a combination thereof. For example, the computer readable medium may include a magnetic medium, an optical recording medium, and a memory. The computer program may be distributed on a networked computer system so that the computer readable code may be stored and executed in a distributed manner. Functional programs, codes, and code segments for implementing the present embodiment may be easily inferred by programmers in the art to which this embodiment belongs.

The present embodiments are provided to explain the technical spirit of the present embodiment and the scope of the technical spirit of the present embodiment is not limited by these embodiments. The protection scope of the present embodiments should be interpreted based on the following appended claims and it should be appreciated that all technical spirits included within a range equivalent thereto are included in the protection scope of the present embodiments.

What is claimed is:

1. A method for training an electrical conductivity reconstruction network for reconstructing a brain electrical conductivity map, comprising:
   generating radio frequency (RF) magnetic field data, current density data, and electric field data using a simulation software and a human head phantom;
   generating a virtual magnetic resonance imaging (MRI) image and a corresponding ground-truth electrical conductivity map from the RF magnetic field data, the current density data, and the electric field data;
   separating the virtual MRI image into real number data and imaginary number data based on generating the virtual MRI image;
   adding noise to the real number data and the imaginary number data, respectively, and integrating noise-added real number data and noise-added imaginary number data to generate noise-added virtual MRI image;
   separating the noise-added virtual MRI image into magnitude data and phase data;
   acquiring patched image kernels from the noise-added virtual MRI image, based on separating the noise-added virtual MRI image; and
   training the electrical conductivity reconstruction network, which is an artificial neural network comprising an input layer, a hidden layer, and an output layer, using the patched image kernels and electrical conductivities of kernel points of the ground-truth electrical conductivity map, which correspond to the patched image kernels, as training data and label data, respectively.

2. The method for training the electrical conductivity reconstruction network according to claim 1, wherein the kernel points correspond to centers of the patched image kernels.

3. The method for training the electrical conductivity reconstruction network according to claim 1, wherein adding noise to the real number data and the imaginary number data use noise having different noise distribution for each training process.

4. The method for training the electrical conductivity reconstruction network according to claim 1, wherein the simulation software is a finite difference time domain (FDTD) simulation software.

5. The method for training the electrical conductivity reconstruction network according to claim 1, wherein the patched image kernels are vectorized to be used as the training data.

* * * * *